United States Patent
Stiehl et al.

(10) Patent No.: US 8,748,622 B2
(45) Date of Patent: Jun. 10, 2014

(54) PROCESS FOR THE PREPARATION OF 4-{4[({[4-CHLORO-3-(TRIFLUOROMETHYL)-PHENYL]AMINO}CARBONYL)AMINO]-3-FLUOROPHENOXY}-N-METHYLPYRIDINE-2-CARBOXAMIDE, ITS SALTS AND MONOHYDRATE

(75) Inventors: Juergen Stiehl, Sprockhövel (DE);
Werner Heilmann, Wuppertal (DE);
Michael Lögers, Wuppertal (DE);
Joachim Rehse, Leichlingen (DE);
Michael Gottfried, Wuppertal (DE);
Saskia Wichmann, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/640,959

(22) PCT Filed: Apr. 8, 2011

(86) PCT No.: PCT/EP2011/055508
§ 371 (c)(1),
(2), (4) Date: Jan. 22, 2013

(87) PCT Pub. No.: WO2011/128261
PCT Pub. Date: Oct. 20, 2011

(65) Prior Publication Data
US 2013/0116442 A1    May 9, 2013

(30) Foreign Application Priority Data

Apr. 15, 2010  (EP) .................................. 10004022

(51) Int. Cl.
*A61K 31/44* (2006.01)
*C07D 213/63* (2006.01)

(52) U.S. Cl.
USPC .......................................... 546/291; 514/350

(58) Field of Classification Search
None
See application file for complete search history.

(56) References Cited

U.S. PATENT DOCUMENTS

| 8,124,630 | B2 | 2/2012 | Riedl et al. |
| 8,124,782 | B2 | 2/2012 | Logers et al. |
| 2003/0181442 | A1 | 9/2003 | Riedl et al. |
| 2005/0038080 | A1 | 2/2005 | Boyer et al. |
| 2008/0262236 | A1 | 10/2008 | Logers et al. |
| 2009/0192127 | A1 | 7/2009 | Scheuring et al. |
| 2010/0173953 | A1 | 7/2010 | Grunenberg et al. |
| 2012/0142742 | A1 | 6/2012 | Riedl et al. |

FOREIGN PATENT DOCUMENTS

| WO | WO-00 42012 | 7/2000 |
| WO | WO-2005 009961 | 2/2005 |
| WO | WO 2005009961 A2 * | 2/2005 |
| WO | WO-2006 034796 | 4/2006 |
| WO | WO-2008 043446 | 4/2008 |
| WO | WO 2008043446 A1 * | 4/2008 |

OTHER PUBLICATIONS

Streitwieser, A. et al., Introduction to Organic Chemistry, New York, Macmillan, 1992, pp. 736-737.*
Bankston, D. et al., "A scaleable synthesis of BAY 43-9006: A Potent Raf Kinase Inhibitor for the Treatment of Cancer," Organic Process Research & Development, 2002, vol. 6, pp. 777-781.
International Search Report for PCT/EP2011/055508, Date of the actual completion of the international search: Jun. 14, 2011, Date of mailing of the international search report: Jun. 21, 2011.

* cited by examiner

*Primary Examiner* — Heidi Reese
(74) *Attorney, Agent, or Firm* — Millen, White, Zelano & Branigan, P.C.

(57) ABSTRACT

The present invention relates to a process for preparing 4-{4-[({[4-chloro-3-(trifluoromethyl)-phenyl]amino}carbonyl)amino]-3-fluorophenoxy}-N-methylpyridine-2-carboxamide, its salts and monohydrate.

11 Claims, No Drawings

PROCESS FOR THE PREPARATION OF 4-{4[({[4-CHLORO-3-(TRIFLUOROMETHYL)-PHENYL]AMINO}CARBONYL)AMINO]-3-FLUOROPHENOXY}-*N*-METHYLPYRIDINE-2-CARBOXAMIDE, ITS SALTS AND MONOHYDRATE

The present invention relates to a process for preparing 4-{4-[({[4-chloro-3-(trifluoromethyl)-phenyl]amino}carbonyl)amino]-3-fluorophenoxy}-N-methylpyridine-2-carboxamide, its salts and monohydrate.

4-{4-[({[4-chloro-3-(trifluoromethyl)phenyl]amino}carbonyl)amino]-3-fluorophenoxy}-N-methylpyridine-2-carboxamide is mentioned in WO 05/009961 and corresponds to the compound of the formula (I):

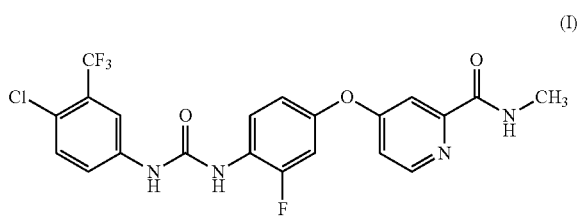 [SMILES: CNC(=O)c1cc(Oc2ccc(NC(=O)Nc3ccc(Cl)c(C(F)(F)F)c3)c(F)c2)ccn1]

The monohydrate of the compound of formula (I) is mentioned in WO 08/043446. Furthermore salts of the compound of formula (I) such as its hydrochloride, mesylate and phenylsulfonate are mentioned in WO 05/009961 and can be formed by treating the compound of the formula (I) with the corresponding acid. The compound of formula (I) is described for treating hyper-proliferative disorders such as cancers, tumors, lymphomas, sarcomas and leukemias.

WO 05/009961 describes a process for preparing the compound of the formula (I), which is illustrated in the following scheme:

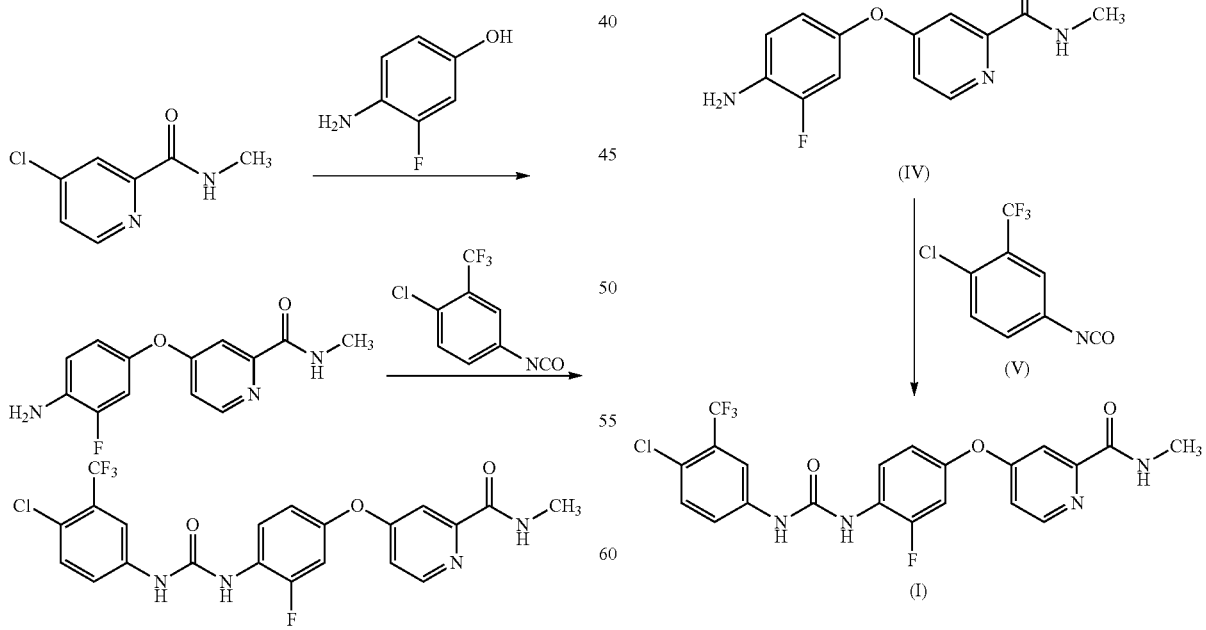

In the first step 4-amino-3-fluorophenol was treated with potassium tert-butoxide and 4-chloro-N-methyl-2-pyridinecarboxamide was added in N,N-dimethylacetamide to form 4-(4-amino-3-fluorophenoxy)pyridine-2-carboxylic acid methylamide which after extraction was finally treated with 4-chloro-3-(trifluoromethyl)phenyl isocyanate in toluene to form 4{4-[3-(4-chloro-3-trifluoromethylphenyl)-ureido]-3-fluorophenoxy}-pyridine-2-carboxylic acid methylamide which is the compound of formula (I).

While the processes disclosed by the prior art are per se effective for preparing the compound of the formula (I), its monohydrate, hydrochloride, mesylate and phenylsulfonate, factors such as purity, product yields, process efficiency, safety and economy are very significant for an industrial scale process of a pharmaceutical product.

It is an object of the present invention to provide a process for preparing the compound of the formula (I), its salts and monohydrate in industrial scale (kilogram to metric tons range) which satisfies the criteria which apply in production and provides improvements in purity, environmental compatibility, industrial employability, safety aspects and volume yield. Especially purity and safety aspects are to be considered for the preparation of pharmaceuticals. This object is achieved by the present invention.

The inventive preparation of the compound of the formula (I) is shown in the following scheme:

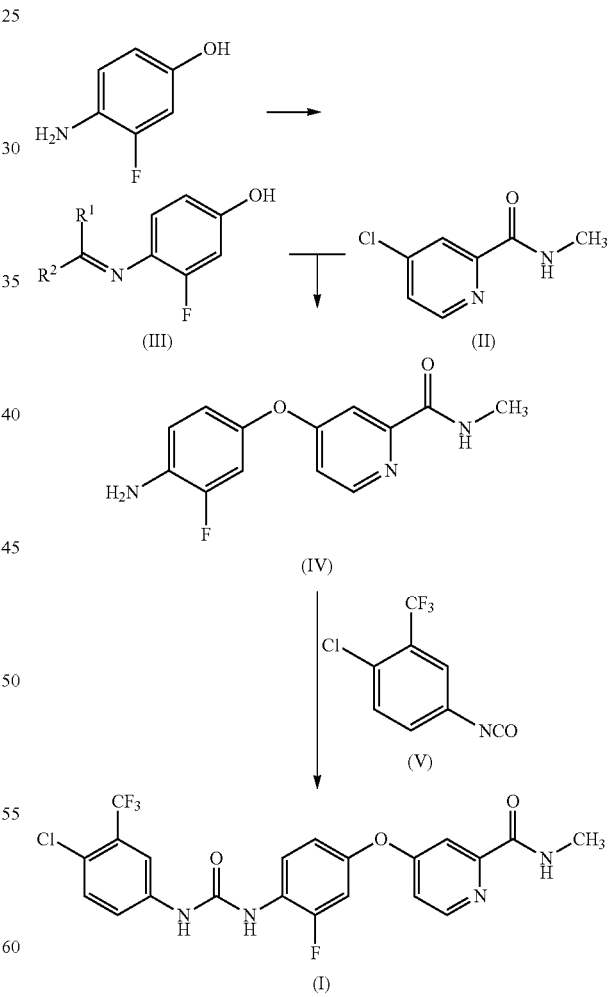

Preparation of the Compound of the Formula (I), its Monohydrate or Salts:

The present invention comprises a process for preparing of the compound of the formula (I)

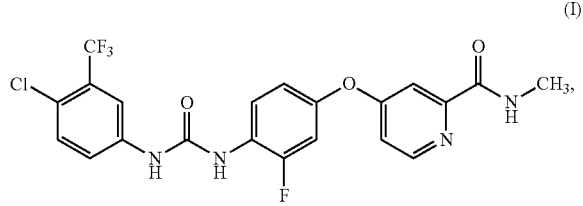 [SMILES: CNC(=O)c1cc(Oc2ccc(NC(=O)Nc3ccc(Cl)c(C(F)(F)F)c3)c(F)c2)ccn1]

(I)

its salt or monohydrate by treating the compound of the formula (IV)

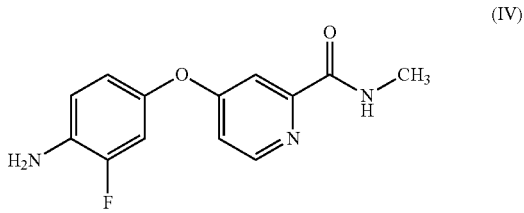 [SMILES: CNC(=O)c1cc(Oc2ccc(N)c(F)c2)ccn1]

(IV)

which is 4-(4-amino-3-fluorophenoxy)-N-methylpyridine-2-carboxamide with the compound of formula (V)

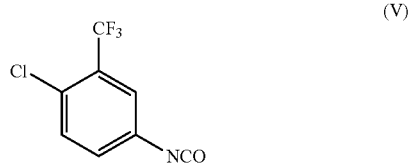

(V)

which is 4-chloro-3-trifluoromethyl-phenyl isocyanate in a reaction mixture and thereafter the solved compound of the formula (I) is treated with an acid to form a salt of the compound of the formula (I) which precipitates from the solution containing the solved compound of the formula (I), optionally the salt of the compound of the formula (I) is then treated with an aqueous basic solution to precipitate the monohydrate of the compound of the formula (I), and optionally the monohydrate is dried under reduced pressure until the compound of the formula (I) is formed.

The salt of the compound of the formula (I) can be prepared by treating the compound of the formula (IV) with the compound of formula (V) in a reaction mixture and thereafter the solved compound of the formula (I) is treated with an acid to form the salt of the compound of the formula (I) which precipitates from the solution containing the solved compound of the formula (I).

The monohydrate of the compound of the formula (I) can be prepared by treating the compound of the formula (IV) with the compound of formula (V) in a reaction mixture and thereafter the solved compound of the formula (I) is treated with an acid to form a salt of the compound of the formula (I) which precipitates from the solution containing the solved compound of the formula (I), the salt of the compound of the formula (I) is then treated with an aqueous basic solution to precipitate the monohydrate of the compound of the formula (I), preferably at a temperature of from 35° C. to 45° C., most preferably from 38° C. to 42° C.

The compound of the formula (I) can be prepared by treating the compound of the formula (IV) with the compound of formula (V) in a reaction mixture and thereafter the solved compound of the formula (I) is treated with an acid to form a salt of the compound of the formula (I) which precipitates from the solution containing the solved compound of the formula (I), the salt of the compound of the formula (I) is then treated with an aqueous basic solution to precipitate the monohydrate of the compound of the formula (I) and the monohydrate is dried under reduced pressure until the compound of the formula (I) is formed, preferably at a temperature of 85° C. to 120° C., and preferably at a pressure of below 30 mbar.

According to the processes described above the solution containing the solved compound of the formula (I) and what from the salt of the compound of the formula (I) precipitates can be preferably the reaction mixture or can be a separate solution containing the compound of the formula (I). The separate solution can be prepared after isolation of the compound of the formula (I) from the reaction mixture for example by standard work-up procedures as described for example in WO 05/009961 and solving the compound of the formula (I) in an suitable organic solvent.

In a preferred embodiment of the process for preparing of the compound of the formula (I), its monohydrate or salt as described above the acid is generated in situ in the solution containing the solved compound of the formula (I) by adding to the reaction mixture a protic substance and an acid precursor.

In a more preferred embodiment of the process for preparing of the compound of the formula (I), its monohydrate or salt the acid is generated in situ in the reaction mixture after the compound of the formula (I) is formed by adding to the reaction mixture an alcohol and an acid precursor.

In a most preferred embodiment of the process for preparing of the compound of the formula (I), its monohydrate or salt the acid is generated in situ in the reaction mixture after the compound of the formula (I) is formed by adding to the reaction mixture an alcohol and an acylchloride, preferably acetylchloride.

In the process for preparing of the compound of the formula (I), its monohydrate or salt the reaction of the compound of the formula (IV) with the compound of the formula (V) is effected in an suitable organic solvent, for example in tetrahydrofuran, at a temperature above 15° C. and below 70° C., preferably at a temperature of from 15° C. to 60° C., more preferably from 15° C. to 50° C., most preferably at room temperature. Preference is given to initially charging the compound of the formula (IV) in a suitable organic solvent, for example in tetrahydrofuran, and admixing within 30 to 300 minutes, preferably within 60 to 150 minutes, most preferably within 80 to 100 minutes the compound of the formula (V), preferably dissolved or suspended in a suitable organic solvent, for example toluene, which can be different to the first suitable organic solvent. After formation of the compound of the formula (I) an acid is added to the reaction mixture. Preferably the acid is generated in situ in the reaction mixture by adding a protic substance for example water and/or an alcohol, preferably an alcohol, and an acid precursor, preferably an acylchloride, within for example 5 to 60 minutes, preferably within 10 to 30 minutes, in order to generate the corresponding acid in situ. Preferably the protic substance is added first. The salt of the compound of the formula (I) can be isolated by precipitation.

In order to prepare the monohydrate of the compound of the formula (I) the salt of the compound of the formula (I) is further treated with an aqueous basic solution, preferably with a mixture of an organic solvent and an aqueous basic solution. The monohydrate of the compound of the formula (I) can be isolated by precipitation, preferably at a temperature of from 35° C. to 45° C., most preferably from 38° C. to 42° C.

In order to prepare the compound of the formula (I) the monohydrate of the compound of the formula (I) is dried preferably at a temperature of 85° C. to 120° C. and under reduced pressure, more preferably at a pressure of below 30 mbar.

Suitable acids in the process for preparing of the compound of the formula (I), its monohydrate or salt include but are not limited to mineral acids, carboxylic acids and sulfonic acids, for example hydrochloric acid, hydrobromic acid, sulfuric acid, phosphoric acid, methanesulfonic acid, trifluoromethanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid. Preference is given to hydrochloric acid, hydrobromic acid, sulfuric acid, phosphoric acid, methanesulfonic acid, trifluoromethanesulfonic acid, ethanesulfonic acid, toluenesulfonic acid, benzenesulfonic acid and naphthalenedisulfonic acid, more preferably to hydrochloric acid, benzenesulfonic acid, toluenesulfonic acid or methanesulfonic acid, most preferably to hydrochloric acid.

Salts of the compound of the formula (I) which are pharmaceutically acceptable salts include but are not limited to acid addition salts of mineral acids, carboxylic acids and sulfonic acids, for example salts of hydrochloric acid, hydrobromic acid, sulfuric acid, phosphoric acid, methanesulfonic acid, trifluoromethanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid. Preference is given to salts of hydrochloric acid, hydrobromic acid, sulfuric acid, phosphoric acid, methanesulfonic acid, trifluoromethanesulfonic acid, ethanesulfonic acid, toluenesulfonic acid, benzenesulfonic acid and naphthalenedisulfonic acid, more preferably to salts of hydrochloric acid, benzenesulfonic acid, toluenesulfonic acid or methanesulfonic acid, most preferably to the hydrochloric acid salt.

According to the present invention alcohols are organic substances carrying at least one hydroxyl group. Alcohols include but are not limited to methanol, ethanol, n-propanol, isopropanol, n-butanol, sec-butanol, isobutanol, n-pentanol, glycerol or a mixture thereof. Preferably methanol, ethanol and isopropanol are used as alcohols in the present process.

In order to prepare the acid in situ suitable acid precursors include but are not limited to organic acid halogenides, preferably acylhalegonides such as acylchlorides and acylbromides, more preferably acetylchloride, a cetylbromide, propionylchloride or propionylbromide, most preferably acetylchloride.

Preference is given to a process described above wherein the acid is prepared in situ without water.

Suitable organic solvents in the process for preparing of the compound of the formula (I), its monohydrate or salt include but are not limited to tetrahydrofuran, toluene, ethyl acetate, dioxane, methyl tert-butyl ether, dimethoxyethane, dimethylsulfoxid, dimethylformamid, 1-methyl-2-pyrrolidinone or mixtures of the mentioned solvents. More preferably tetrahydofuran, toluene and mixtures thereof are used.

Suitable aqueous basic solutions in the process for preparing of the monohydrate of the compound of the formula (I) include but are not limited to aqueous solutions of alkali metal hydroxides, alkali earth metal hydroxides, alkali metal alkoxides, alkali earth metal alkoxides, organic amines and ammonia, preferably sodium hydroxide and potassium hydroxide, more preferably an aqueous solution of sodium hydroxide. The aqueous basic solution can be mixed with an organic solvent such as acetone, ethyl acetate, tetrahydrofuran, preferably with acetone.

According to the present process potential side products, in particular anilinic side products such as the starting compounds 4-amino-3-fluorophenol and the compound of the formula (IV) can be separated very effectively form the salt of the compound of the formula (I), preferably the hydrochloric acid salt, because the salts of the anilinic side products, in particular the salts of the compound of the formula (IV), preferably the hydrochloric acid salt of the compound of the formula (IV), do not precipitate under the conditions according to the present process and remain in the filtrate. Furthermore in the case when the acid is generated in situ by using acylhalogenides the corresponding acylated derivatives of the anilinic side products, in particular of the compound of the formula (IV), can be separated easily from the salt of the compound of the formula (I), preferably the hydrochloric acid salt, because the acylated derivatives do not precipitate under the conditions according to the present process and remain in the filtrate. Therefore the compound of the formula (I), its salts and its monohydrate can be prepared in a very high purity.

Another embodiment of the present invention is the compound of formula (I), its monohydrate or salt in a very high purity containing or contaminated with one or more anilinic substances each in an amount of equal or less than 0.05%, that means from 0.0001% to a maximum of 0.05%, preferably each in an amount of equal or less than 0.025%, that means from 0.0001% to a maximum of 0.025%, most preferably each in an amount of equal or less than 0.01%, that means from 0.0001% to a maximum of 0.01% by weight based on the amount of the compound of the formula (I). In other words the another embodiment is a mixture of the compound of formula (I), its monohydrate or salt with one or more anilinic substances each anilinic substance in an amount of equal or less than 0.05%, that means from 0.0001% to a maximum of 0.05%, preferably each in an amount of equal or less than 0.025%, that means from 0.0001% to a maximum of 0.025%, most preferably each in an amount of equal or less than 0.01%, that means from 0.0001% to a maximum of 0.01% by weight based on the amount of the compound of the formula (I)

Anilinic substances include but are not limited to 4-amino-3-fluorophenol, 4-chloro-3-trifluoromethylaniline, 4-(4-amino-3-fluorophenoxy)pyridine-2-carboxylic acid methylamide which is the compound of the formula (IV).

Preference is given to the compound of formula (I), its monohydrate or salt containing or contaminated with 4-amino-3-fluorophenol and/or 4-(4-amino-3-fluorophenoxy)pyridine-2-carboxylic acid methylamide each in an amount of equal or less than 0.05%, that means from 0.0001% to a maximum of 0.05%, preferably each in an amount of equal or less than 0.025%, that means from 0.0001% to a maximum of 0.025%, most preferably each in an amount of equal or less than 0.01%, that means from 0.0001% to a maximum of 0.01% by weight based on the amount of the compound of the formula (I). In other words preference is given to a mixture of the compound of formula (I), its monohydrate or salt with 4-amino-3-fluorophenol and/or 4-(4-amino-3-fluorophenoxy)pyridine-2-carboxylic acid methylamide each anilinic substance in an amount of equal or less than 0.05%, that means from 0.0001% to a maximum of 0.05%, preferably each in an amount of equal or less than 0.025%, that means from 0.0001% to a maximum of 0.025%, most preferably each in an amount of equal or less than 0.01%, that means from 0.0001% to a maximum of 0.01% by weight based on the amount of the compound of the formula (I).

Preparation of the Compound of the Formula (IV):

The present invention likewise comprises a process for preparing the compound of the formula (IV) by reacting the compound of the formula (III)

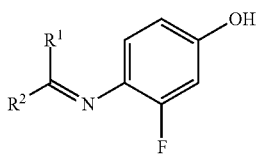

(III)

wherein R¹ and R² are independently selected from the group consisting of hydrogen, methyl, ethyl, n-propyl, iso-propyl, n-butyl, iso-butyl, sec-butyl, tert-butyl, n-pentyl, 2-pentyl, 3-pentyl, neopentyl, n-hexyl, 2-hexyl and 3-hexyl, or R¹ and R² are joined and, taken together with the carbon atom to which they are attached, form a 4- to 7-membered cycloalkyl ring.

with the compound of the formula (II)

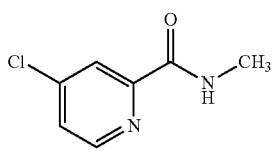

(II)

which is 4-chloro-N-methyl-2-pyridinecarboxamide in the presence of a base, followed by adding an acid to deliver the compound of the formula (IV).

In a preferred embodiment of the process for preparing of the compound of the formula (IV) the compound of the formula (III) is used in a solution of a suitable organic solvent and is formed by reacting 4-amino-3-fluorophenol with the compound of the formula (VI)

(VI)

wherein R¹ and R² are independently selected from the group consisting of hydrogen, methyl, ethyl, n-propyl, iso-propyl, n-butyl, iso-butyl, sec-butyl, tert-butyl, n-pentyl, 2-pentyl, 3-pentyl, neopentyl, n-hexyl, 2-hexyl and 3-hexyl, or R¹ and R² are joined and, taken together with the carbon atom to which they are attached, form a 4- to 7-membered cycloalkyl ring.

In a further preferred embodiment of the process for preparing of the compound of the formula (IV) the compound of the formula (II) is used in a solution of a suitable organic solvent which solution is prepared by neutralization the hydrochloric acid salt of the compound of the formula (II) with a base, preferably with sodium hydroxide, more preferably with an aqueous solution of sodium hydroxide.

In the process for preparing of the compound of the formula (IV) 4-amino-3-fluorophenol reacts with the compound of formula (VI) at a temperature of from 20° C. up to reflux temperature, preferably from 50° C. up to reflux temperature, most preferably at the reflux temperature of the compound of formula (VI) which can be used in excess and as solvent. Optionally a further different solvent can be added such as toluene, ethyl acetate, cyclohexane or a mixture thereof. The volatile reaction components can be removed by azeotropic distillation optionally under reduced pressure. The formed compound of the formula (III) can be used in a solution of a suitable organic solvent, preferably in a solution of 1-methyl-2-pyrrolidinone, and is treated with 4-chloro-N-methyl-2-pyridinecarboxamide, preferably used in a solution with a suitable organic solvent, more preferably in a solution of 1-methyl-2-pyrrolidinone, in the presence of a base. The reaction mixture is heated to a temperature of from 50° C. up to 150° C., preferably from 80° C. up to 120° C. After 1 to 5 h, preferably 2 to 4 h, the temperature is adjusted to from 50° C. up to 90° C., preferably from 70° C. up to 90° C., and an acid, preferably acetic acid in water, is added. After cooling, preferably to a temperature of from 0° C. to 10° C., and optionally seeding with crystals of the compound of the formula (IV), the compound of the formula (IV) can be isolated by precipitation.

Preference is given to a compound of the formula (VI) wherein R¹ and R² are independently selected from methyl, ethyl, n-propyl, iso-propyl, n-butyl, iso-butyl, sec-butyl or R¹ and R² are joined and, taken together with the carbon atom to which they are attached, form a 4- to 7-membered cycloalkyl ring. More preferably the compound of the formula (VI) is selected from the group consisting of 4-methyl-2-pentanone, 3-methyl-2-butanone, 2-butanone, 2-pentanone, 4-heptanone, 2,4-dimethyl-3-pentanone and cyclohexanone.

Suitable organic solvents in the process for preparing of the compound of the formula (IV) include but are not limited to 1-methyl-2-pyrrolidinone, dimethylformamide, N,N-dimethylacetamid, dimethyl sulfoxide, sulfolane or mixtures of the solvents mentioned. Preferably 1-methyl-2-pyrrolidinone and/or dimethylformamide are used.

In the process for preparing of the compound of the formula (IV) suitable bases are alkali metal hydroxides and alkali metal alkoxides. Preference is given to potassium tert-butoxide. Potassium tert-butoxide is preferably used in a solution, more preferably in a tetrahydrofuran solution.

In order to provide a highly purified version of the compound of the formula (II) it is solved in a suitable organic solvent, treated with an acid which is generated in situ by adding a protic substance and an acid precursor, precipitated as a salt of the compound of the formula (II), preferably the hydrochloric acid salt of the compound of the formula (II), and neutralized by adding an aqueous solution of a base.

For that purpose the starting compound 4-chloro-N-methyl-2-pyridinecarboxamide is solved in a suitable organic solvent, preferably in toluene, and is treated with an acid which is generated in situ by adding a protic substance, for example water and/or an alcohol, preferably an alcohol, and an acid precursor, preferably an acylchloride, for example within 5 to 60 minutes, preferably within 10 to 30 minutes, in order to generate the corresponding acid in situ. Preferably the protic substance is added first. The salt of 4-chloro-N-methyl-2-pyridinecarboxamide, preferably the hydrochloric acid salt of 4-chloro-N-methyl-2-pyridinecarboxamide, can be isolated by precipitation. Such purified salt of 4-chloro-N-methyl-2-pyridinecarboxamide is solved in a suitable organic solvent, preferably in toluene, and is neutralized by adding an aqueous solution of a base, preferably an aqueous solution of sodium hydroxide. After separation of the phases the organic phase is optionally concentrated under reduced pressure and a suitable organic solvent, preferably 1-methyl-2-pyrrolidinone, is added to prepare a solution which can be used directly for the preparation of the compound of the formula (IV) as described above.

Suitable organic solvents in the process for preparing of 4-chloro-N-methyl-2-pyridinecarboxamide include but are not limited to tetrahydrofuran, toluene, ethyl acetate, dioxane, methyl tert-butyl ether, dimethoxyethane, dimethylsulfoxid, dimethylformamid, 1-methyl-2-pyrrolidinone or mixtures of the mentioned solvents. More preferably tetrahydofuran, toluene and mixtures thereof are used.

According to the present invention alcohols are organic substances carrying at least one hydroxyl group. Alcohols include but are not limited to methanol, ethanol, n-propanol, isopropanol, n-butanol, sec-butanol, isobutanol, n-pentanol, glycerol or a mixture thereof. Preferably methanol, ethanol, isopropnaol are used as alcohols in the present process.

In order to prepare the acid in situ suitable precursors include but are not limited to organic acid halogenides, preferably acylhalegonides such as acylchlorides and acylbromides, more preferably acetylchloride, acteylbromide, propionylchloride or propionylbromide, most preferably acetylchloride.

Preference is given to an in situ preparation of the acid without water.

Alternatively the compound of formula (II) and its hydrochloric acid salt can be prepared as described in WO 05/009961 or in Bankston et al. (Organic Process Research & Development, 2002, 6, 777-781).

The compound of the formula (V) which is 4-chloro-3-trifluoromethyl-phenylisocyanate can be prepared as described in WO 00/42012.

| Abbreviations: | |
|---|---|
| DCI | direct chemical ionization (in MS) |
| DMF | dimethylformamide |
| DMSO | dimethyl sulfoxide |
| EI | electron impact ionization (in MS) |
| ESI | electrospray ionization (in MS) |
| h | hour(s) |
| min | minute(s) |
| m.p. | melting point |
| MS | mass spectrometry |
| NMR | nuclear resonance spectroscopy |
| THF | tetrahydrofuran |

WORKING EXAMPLES $^1$H-NMR spectra were recorded at room temperature using spectrometers from Bruker. Deuterium dimethylsulfoxide was used as solvent including tetramethylsilan as internal standard (if not otherwised mentioned).

MS spectra were recorded using spectrometers from Waters and Applied Biosystems. The relative signal intensity is stated (in percent based on the basis peak).

HPLC was performed using HP 1100 from Hewlett Packard. The definite conditions are stated with the respective working examples.

Preparation of 4-{4-[({[4-chloro-3-(trifluoromethyl)-phenyl]amino}carbonyl)amino]-3-fluorophenoxy}-N-methylpyridine-2-carboxamide, its hydrochloride and its monohydrate Stage 1

4-chloro-N-methyl-pyridine-2-carboxamide hydrochloride 420 g of a solution of 4-chloro-N-methylpyridine-2-carboxamide (prepared according to WO2006/034796) in toluene (approx. 30% w/w) and 48.8 g of ethanol were charged into a reaction flask. 67.2 g of acetyl chloride was added with stirring to such a degree that the temperature of the reaction mixture did not exceed 30° C. After stirring further at room temperature for 1.5 h the product was filtered off, washed with toluene (212 g) and dried under reduced pressure (30° C., 80 mbar). In this way 156 g (quantitative yield) of 4-chloro-N-methyl-pyridine-2-carboxamide hydrochloride were obtained.

m.p. 173.5-174.5° C.

$^1$H-NMR (500 MHz, DMSO-d$_6$): δ [ppm]=2.93 (d, 3H), 7.79-7.97 (m, 1H), 8.13-8.26 (m, 1H), 8.71 (d, 1H), 9.03 (br. s., 1H), 13.16 (br. s., 1H).

MS [DCI, NH3]: m/e=171 [M+H]$^+$ (M=free base).

HPLC: stationary phase: Nucleodur Gravity C18 (150 mm length, 3 mm ID, 3.0 µm particle size); mobile phase A: 1.15 g di-ammoniumhydrogenphosphate+0.68 mL o-phosphoric acid (85% in water)/1 L water; mobile phase B: acetonitrile; UV detection at 254 nm; oven temperature: 45° C., injection volume: 3 µl, flow: 0.5 mL/min.; linear gradient: 5% B→80% B (20 min.), 10 minutes holding time at 80% B; purity: >98% (Rt=17.9 min.).

Stage 2

4-(4-amino-3-fluorophenoxy)-N-methylpyridine-2-carboxamide

Method 2a:

A reaction flask with stirrer was charged with 41.4 g of 4-chloro-N-methyl-pyridine-2-carboxamide hydrochloride and 100 g of toluene as solvent. After addition of 68.4 g of water and 19.6 g of an aqueous sodium hydroxide solution (45% w/w) the reaction mixture was stirred for 30 minutes. The two phases were separated and the aqueous layer was discarded. The organic layer was concentrated by distillation under vacuum and toluene was substituted by 1-methyl-2-pyrrolidinone (70 g) to yield a solution of 4-chloro-N-methyl-pyridine-2-carboxamide in 1-methyl-2-pyrrolidinone.

A second reaction flask with stirrer was charged with 26.7 g of 4-amino-3-fluorophenol and 100 g of 4-methyl-2-pentanone. By heating to reflux and additional stirring for 1 hour water was removed by azeotropic distillation. Then the excess 4-methyl-2-pentanone was removed by distillation under vacuum and substituted by 1-methyl-2-pyrrolidinone (70 g) to prepare a solution containing the imin compound according to formula (III). To the resulting reaction mixture the solution of 4-chloro-N-methyl-pyridine-2-carboxamide in 1-methyl-2-pyrrolidinone was added. The reaction mixture was heated to approximately 100° C. 123.2 g of potassium-t-butoxide in tetrahydrofuran (20% w/w) was added dropwise (within approx. 70 minutes) whilst tetrahydrofuran was removed by distillation. Thereafter the reaction mixture was stirred for additional 3 hours at 100° C. to complete the reaction. After adjusting to 80° C. 350 ml of toluene, of 392 ml water and 8 g of acetic acid were added. The mixture was stirred for 10 minutes at 80° C., cooled down to 50° C. and seeded with crystals of 4-(4-amino-3-fluorophenoxy)-N-methylpyridine-2-carboxamide. After cooling to 0° C. the suspension was stirred for approximately 30 minutes. The product was filtered off, washed with methanol/water (1:3 v/v, 144 ml) and dried under reduced pressure (30° C., 80 mbar). In this way 40.7 g (78% of theory) of 4-(4-amino-3-fluorophenoxy)-N-methylpyridine-2-carboxamide were obtained as brown crystals.

m.p. 140.5-141.2° C.

$^1$H-NMR (400 MHz, DMSO-$d_6$): δ [ppm]=2.86 (d, 3H), 5.24-5.35 (s, 2H), 6.80-6.86 (m, 1H), 6.89-6.99 (m, 1H), 7.01-7.09 (m, 1H), 7.09-7.15 (m, 1H), 7.45 (d, 1H), 8.49 (d, 1H), 8.75-8.85 (m, 1H).

MS [ES]: m/e=262 [M+H]$^+$

HPLC: stationary phase: Agilent Zorbax SB-AQ (150 mm length, 3 mm ID, 3.5 μm particle size); mobile phase A: 1.40 g di-potassiumhydrogenphosphat+5.8 ml o-phosphoric acid (8.5% in water)/1 L water; mobile phase B: acetonitrile; UV detection at 268 nm; oven temperature: 50° C., injection volume: 3 μl, flow: 0.8 mL/min; linear gradient in two steps: 10% B→37% B (10 min.), 37% B→80% B (10 min.), 10 minutes holding time at 80% B; purity: >97% (Rt=9.2 min.).

Method 2b:

A reaction flask with stirrer was charged with 41.4 g of 4-chloro-N-methyl-pyridine-2-carboxamide hydrochloride and 100 g of toluene as solvent. After addition of 68.4 g of water and 19.6 g of an aqueous sodium hydroxide solution (45% w/w) the reaction mixture was stirred for 30 minutes. The two phases were separated and the aqueous layer was discarded. The organic layer was concentrated by distillation under vacuum and toluene was substituted by 1-methyl-2-pyrrolidinone (70 g) to yield a solution of 4-chloro-N-methyl-pyridine-2-carboxamide in 1-methyl-2-pyrrolidinone.

A second reaction flask with stirrer was charged with 26.7 g of 4-amino-3-fluorophenol and 100 g of 3-methyl-2-butanone. By heating to reflux and additional stirring for 3 hours water was removed by azeotropic distillation. Then the excess 3-methyl-2-butanone was removed by distillation under vacuum and substituted by 1-methyl-2-pyrrolidinone (70 g) to prepare a solution containing the imin compound according to formula (III). To the resulting reaction mixture the solution of 4-chloro-N-methyl-pyridine-2-carboxamide in 1-methyl-2-pyrrolidinone was added. The reaction mixture was heated to approximately 100° C. 123.2 g of potassium-t-butoxide in tetrahydrofuran (20% w/w) was added dropwise (within approx. 3 hours) whilst tetrahydrofuran was removed by distillation. Thereafter the reaction mixture was stirred for additional 2.5 hours at 100° C. to complete the reaction. After adjusting to 80° C. 350 ml of toluene of 392 ml water and of 8 g acetic acid were added. The mixture was stirred for 10 minutes at 80° C., cooled down to 50° C. and seeded with crystals of 4-(4-amino-3-fluorophenoxy)-N-methylpyridine-2-carboxamide. After cooling to 0° C. the suspension was stirred for approximately 30 minutes. The product was filtered off, washed with methanol/water (1:3 v/v, 144 ml) and dried under reduced pressure (30° C., 80 mbar). In this way 44.4 g (84% of theory) of 4-(4-amino-3-fluorophenoxy)-N-methylpyridine-2-carboxamide were obtained as light brown crystals.

m.p. 142.2-142.8° C.

$^1$H-NMR (400 MHz, DMSO-$d_6$): δ [ppm]=2.83 (d, 3H), 5.27 (s, 2H), 6.78-6.85 (m, 1H), 6.86-6.94 (m, 1H), 7.01-7.07 (m, 1H), 7.09-7.14 (m, 1H), 7.41 (d, 1H), 8.49 (d, 1H), 8.71-8.87 (m, 1H).

MS [ES]: m/e=262 [M+H]$^+$

HPLC: stationary phase: Agilent Zorbax SB-AQ (150 mm length, 3 mm ID, 3.5 μm particle size); mobile phase A: 1.40 g di-potassiumhydrogenphosphat+5.8 ml o-phosphoric acid (8.5% in water)/1 L water; mobile phase B: acetonitrile; UV detection at 268 nm; oven temperature: 50° C., injection volume: 3 μl, flow: 0.8 mL/min; linear gradient in two steps: 10% B→37% B (10 min.), 37% B→80% B (10 min.), 10 minutes holding time at 80% B; purity: >99% (Rt=9.1 min.).

Method 2c:

A reaction flask with stirrer was charged with 41.4 g of 4-chloro-N-methyl-pyridine-2-carboxamide hydrochloride and 100 g of toluene as solvent. After addition of 68.4 g of water and 19.6 g of an aqueous sodium hydroxide solution (45% w/w) the reaction mixture was stirred for 30 minutes. The two phases were separated and the aqueous layer was discarded. The organic layer was concentrated by distillation under vacuum and toluene was substituted by 1-methyl-2-pyrrolidinone (70 g) to yield a solution of 4-chloro-N-methyl-pyridine-2-carboxamide in 1-methyl-2-pyrrolidinone.

A second reaction flask with stirrer was charged with 26.7 g of 4-amino-3-fluorophenol, 73 g of cyclohexane and 20.6 g of cyclohexanone. By heating to reflux and additional stirring for 3 hours water was removed by azeotropic distillation. Then the solvent cyclohexane and the excess cyclohexanone was removed by distillation under vacuum and substituted by 1-methyl-2-pyrrolidinone (70 g) to prepare a solution containing the imin compound according to the formula (III). To the resulting reaction mixture the solution of 4-chloro-N-methyl-pyridine-2-carboxamide in 1-methyl-2-pyrrolidinone was added. The reaction mixture was heated to approximately 100° C. 126 g of potassium-t-butoxide in tetrahydrofuran (20% w/w) was added dropwise (within approx. 40 minutes) whilst tetrahydrofuran was removed by distillation. Thereafter the reaction mixture was stirred for additional 3 hours at 100° C. to complete the reaction. After adjusting to 80° C. 350 ml of toluene, of 392 ml water and of 8 g acetic acid were added. The mixture was stirred for 10 minutes at 80° C., cooled down to 50° C. and seeded with crystals of 4-(4-amino-3-fluorophenoxy)-N-methylpyridine-2-carboxamide. After cooling to 3° C. the suspension was stirred for approximately 30 minutes. The product was filtered off, washed with methanol/water (1:3 v/v, 144 ml) and dried under reduced pressure (30° C., 80 mbar). In this way 40.2 g (76% of theory) of 4-(4-amino-3-fluorophenoxy)-N-methylpyridine-2-carboxamide were obtained as light brown crystals.

m.p. 141° C.

1H-NMR (400 MHz, DMSO-d6): δ [ppm]=2.83 (d, 3H), 5.27 (s, 2H), 6.78-6.85 (m, 1H), 6.86-6.94 (m, 1H), 7.01-7.07 (m, 1H), 7.09-7.14 (m, 1H), 7.41 (d, 1H), 8.49 (d, 1H), 8.71-8.87 (m, 1H).

MS [ES]: m/e=262 [M+H]+

HPLC: stationary phase: Agilent Zorbax SB-AQ (150 mm length, 3 mm ID, 3.5 μm particle size); mobile phase A: 1.40 g di-potassiumhydrogenphosphat+5.8 ml o-phosphoric acid (8.5% in water)/1 L water; mobile phase B: acetonitrile; UV detection at 268 nm; oven temperature: 50° C., injection volume: 3 μl, flow: 0.8 mL/min; linear gradient in two steps: 10% B→37% B (10 min.), 37% B→80% B (10 min.), 10 minutes holding time at 80% B; purity: >98% (Rt=9.1 min.).

Stage 3

4-{4-[({[4-chloro-3-(trifluoromethyl)-phenyl]amino}carbonyl)amino]-3-fluorophenoxy}-N-methylpyridine-2-carboxamide monohydrate A reaction flask with stirrer was charged with 20.0 g of 4-(4-amino-3-fluorophenoxy)-N-methylpyridine-2-carboxamide and 180 g of tetrahydrofuran as solvent. A solution of 18.7 g of 4-chloro-3-trifluoromethyl-phenylisocyanate and 21.1 g of toluene was added dropwise within approximately 90 minutes at room temperature. The resulting solution was stirred for 3 hours to complete the reaction. After then 30 g of tetrahydrofuran and 7.8 g of methanol were added to the reaction mixture. Following 9.0 g of acetyl chloride were added dropwise within 15 minutes to the reaction mixture. After additional stirring for approximately 2 hours the suspension was filtered and the solid was washed with tetrahydofuran (18.2 g) and acetone (136.4 g). The solid was added to a mixture of acetone (268.6 g), water (55.8 g) and an aqueous sodium hydroxide solution (8.2 g, 45% w/w) at 40° C. The mixture was stirred for additional 30 minutes. Then the crystallization was initiated by seeding with crystals of 4-{4-[({[4-chloro-3-(trifluoromethyl)-phenyl]amino}carbonyl)amino]-3-fluorophenoxy}-N-methylpyridine-2-carboxamide monohydrate. After cooling to 20° C. 31.6 g of water were added. The suspension was cooled down to approx. 3° C. and stirred for 30 minutes. The product was filtered off, washed with a cold mixture of acetone (106 g) and water (44 g) and dried under reduced pressure (30° C., 80 mbar). In this way 31.8 g (83% of theory) of 4-{4-[({[4-chloro-3-(trifluoromethyl)-phenyl]amino}carbonyl)amino]-3-fluorophenoxy}-N-methylpyridine-2-carboxamide monohydrate were obtained as white crystals.

1H-NMR (500 MHz, METHANOL-d4): δ [ppm]=2.94 (s, 3H), 6.96-7.01 (m, 1H), 7.05-7.11 (m, 2H), 7.49-7.53 (m, 1H), 7.56-7.59 (m, 1H), 7.61-7.65 (m, 1H), 8.00-8.03 (m, 1H), 8.15-8.20 (m, 1H), 8.46-8.51 (m, 1H).

MS [ES]: m/e=483 [M+H]$^+$

HPLC: stationary phase: Eclipse XDB-C8 (150 mm length, 2.1 mm ID, 3.5 μm particle size); mobile phase A: 1.0 g hexane-1-sulfonic acid sodium salt+1.0 mL trifluoro acetic acid/1 L water; mobile phase B: acetonitrile; UV detection at 232 nm; oven temperature: 43° C., injection volume: 3 μl, flow: 0.5 mL/min; linear gradient in 3 steps: 5% B→36% B (14.5 min.), 36% B→44% B (6 min.), 44% B→80% B (9.5 min.), 10 minutes holding time at 80% B; purity: >99.5% (Rt=25.7 min.), relevant potential by-products: 4-amino-3-fluorophenol at RRT (relative retention time) of 0.10: typically <0.01% (2.6 min.), 4-(4-amino-3-fluorophenoxy)-N-methylpyridine-2-carboxamide RRT 0.37: typically <0.01% (9.5 min.); RRT 0.46 (4-(3-Fluoro-4-{[2-(methylcarbamoyl)pyridin-4-yl]amino}phenoxy)-N-methylpyridine-2-carboxamide): typically <0.15% (11.7 min.); RRT 0.69 (4-(3-fluoro-4-{[(2-fluoro-4-{[2-(methylcarbamoyl)pyridin-4-yl]oxy}phenyl)carbamoyl]ami¬no}phenoxy)-N-methylpyridine-2-carboxamide): typically <0.15% (17.7 min.).

HPLC (trace analysis method for quantification of 4-amino-3-fluorophenol): stationary phase: X-Bridge Shield C18 (150 mm length, 3.0 mm ID, 3.5 μm particle size); mobile phase A: 1.5 g potassium dihydrogenphosphate+0.5 g dipotassium hydrogenphosphate 1 L water; mobile phase B: acetonitrile; UV detection at 228 nm; oven temperature: 50° C., injection volume: 3 μl, flow: 1.0 mL/min; 5 minutes holding time at 5% B, linear gradient in 1 step: 5% B→80% B (10 min.), RT of 4-amino-3-fluorophenol: 1.7 min., quantification against external standard of 4-amino-3-fluorophenol.

HPLC (trace analysis method for quantification of 4-(4-amino-3-fluorophenoxy)-N-methylpyridine-2-carboxamide): stationary phase: X-Bridge Shield C18 (150 mm length, 3.0 mm ID, 3.5 μm particle size); mobile phase A: 1.5 g potassium dihydrogenphosphate+0.5 g dipotassium hydrogenphosphate 1 L water; mobile phase B: acetonitrile; UV detection at 228 nm; oven temperature: 50° C., injection volume: 3 μl, flow: 1.0 mL/min; linear gradient in 1 step: 8% B→80% B (15 min.), RT of 4-(4-amino-3-fluorophenoxy)-N-methylpyridine-2-carboxamide: 7.0 min., quantification against external standard of 4-(4-amino-3-fluorophenoxy)-N-methylpyridine-2-carboxamide.

Stage 4

4-{4-[({[4-chloro-3-(trifluoromethyl)-phenyl]amino}carbonyl)amino]-3-fluorophenoxy}-N-methylpyridine-2-carboxamide 10.2 g of 4-{4-[({[4-chloro-3-(trifluoromethyl)-phenyl]amino}carbonyl)amino]-3-fluorophenoxy}-N-methylpyridine-2-carboxamide monohydrate was dried under reduced pressure (21 mbar) at 90° C. for 3 hours. In this way 9.8 g of 4-{4-[({[4-chloro-3-(trifluoromethyl)-phenyl]amino}carbonyl)-amino]-3-fluorophenoxy}-N-methylpyridine-2-carboxamide were obtained as white crystals.

m.p. 187-188° C.

$^1$H-NMR (400 MHz, METHANOL-d$_4$): δ [ppm]=2.94 (s, 3H), 6.94-7.13 (m, 3H), 7.51 (d, 1H), 7.58 (d, 1H), 7.61-7.67 (m, 1H), 8.01 (d, 1H), 8.17 (t, 1H), 8.45-8.53 (m, 1H).

MS [ES]: m/e=483 [M+H]$^+$

HPLC: stationary phase: Eclipse XDB-C8 (150 mm length, 2.1 mm ID, 3.5 μm particle size); mobile phase A: 1.0 g hexane-1-sulfonic acid sodium salt+1.0 mL trifluoro acetic acid/1 L water; mobile phase B: acetonitrile; UV detection at 232 nm; oven temperature: 43° C., injection volume: 3 μl, flow: 0.5 mL/min; linear gradient in 3 steps: 5% B→36% B (14.5 min.), 36% B→44% B (6 min.), 44% B→80% B (9.5 min.), 10 minutes holding time at 80% B; purity: >99.5% (Rt=25.2 min.), relevant potential by-products: 4-amino-3-fluorophenol at RRT (relative retention time) of 0.10: typically <0.01% (2.5 min.), 4-(4-amino-3-fluorophenoxy)-N-methylpyridine-2-carboxamide RRT 0.36: typically <0.01% (9.1 min.); RRT 0.46 (4-(3-Fluoro-4-{[2-(methylcarbamoyl)pyridin-4-yl]amino}phenoxy)-N-methylpyridine-2-carboxamide): typically <0.15% (11.3 min.); RRT 0.69 (4-(3-fluoro-4-{[(2-fluoro-4-{[2-(methylcarbamoyl)pyridin-4-yl]oxy}phenyl)carbamoyl]ami¬no}phenoxy)-N-methylpyridine-2-carboxamide): typically <0.15% (17.2 min.).

HPLC (trace analysis method for quantification of 4-amino-3-fluorophenol): stationary phase: X-Bridge Shield C18 (150 mm length, 3.0 mm ID, 3.5 μm particle size); mobile phase A: 1.5 g potassium dihydrogenphosphate+0.5 g dipotassium hydrogenphosphate 1 L water; mobile phase B: acetonitrile; UV detection at 228 nm; oven temperature: 50° C., injection volume: 3 μl, flow: 1.0 mL/min; 5 minutes holding time at 5% B, linear gradient in 1 step: 5% B→80% B (10 min.), RT of 4-amino-3-fluorophenol: 1.7 min., quantification against external standard of 4-amino-3-fluorophenol.

HPLC (trace analysis method for quantification of 4-(4-amino-3-fluorophenoxy)-N-methylpyridine-2-carboxamide): stationary phase: X-Bridge Shield C18 (150 mm length, 3.0 mm ID, 3.5 μm particle size); mobile phase A: 1.5 g potassium dihydrogenphosphate+0.5 g dipotassium hydrogenphosphate 1 L water; mobile phase B: acetonitrile; UV detection at 228 nm; oven temperature: 50° C., injection volume: 3 μl, flow: 1.0 mL/min; linear gradient in 1 step: 8% B→80% B (15 min.), RT of 4-(4-amino-3-fluorophenoxy)-N-methylpyridine-2-carboxamide: 7.0 min., quantification against external standard of 4-(4-amino-3-fluorophenoxy)-N-methylpyridine-2-carboxamide.

What is claimed is:

1. A process for preparing the compound of the formula (I)

(I)

[Structure of compound (I): 4-chloro-3-(trifluoromethyl)phenyl urea linked to 2-fluoro-4-(pyridin-4-yloxy)phenyl with N-methylcarboxamide]

or its monohydrate by treating the compound of the formula (IV)

(IV)

[Structure of compound (IV): 4-amino-3-fluorophenyl linked via oxygen to pyridine-2-carboxylic acid methylamide]

with the compound of formula (V)

(V)

[Structure of compound (V): 4-chloro-3-(trifluoromethyl)phenyl isocyanate]

in a reaction mixture and thereafter the dissolved compound of the formula (I) in solution is treated with an acid to form a salt of the compound of the formula (I) which precipitates from the solution containing the dissolved compound of the formula (I), and said salt of the compound of the formula (I) is then treated with an aqueous basic solution to precipitate the monohydrate of the compound of the formula (I), optionally said monohydrate is dried under reduced pressure until the compound of the formula (I) is formed.

2. The process of claim 1 wherein the monohydrate of the compound of the formula (I) precipitates at a temperature of from 35° C. to 45° C.

3. The process of claim 1 for preparing of the compound of the formula (I) wherein the monohydrate is dried under reduced pressure until the compound of the formula (I) is formed.

4. The process of claim 1 wherein the acid is generated in situ in the reaction mixture after the compound of the formula (I) is formed by adding to the reaction mixture a protic substance and an acid precursor.

5. The process of claim 4 wherein the acid is generated in situ in the reaction mixture after the compound of the formula (I) is formed by adding to the reaction mixture an alcohol and an acylchloride.

6. The process of claim 5 wherein the alcohol is ethanol and the acylchloride is acetylchloride.

7. The process of claim 1 wherein the compound of the formula (IV) is prepared by reacting the compound of the formula (III)

(III)

[Structure of compound (III): imine-substituted 2-fluoro-4-hydroxyphenyl]

wherein $R^1$ and $R^2$ are independently selected from the group consisting of hydrogen, methyl, ethyl, n-propyl, iso-propyl, n-butyl, iso-butyl, sec-butyl, tert-butyl, n-pentyl, 2-pentyl, 3-pentyl, neopentyl, n-hexyl, 2-hexyl and 3-hexyl, or $R^1$ and $R^2$ are joined and, taken together with the carbon atom to which they are attached, form a 4- to 7-membered cycloalkyl ring, with the compound of the formula (II)

(II)

[Structure of compound (II): 4-chloropyridine-2-carboxylic acid methylamide]

in the presence of a base, followed by adding an acid to deliver the compound of the formula (IV).

8. The process of claim 7 wherein the compound of the formula (III) is used in a solution of a suitable organic solvent and is formed by reacting 4-amino-3-fluorophenol with the compound of the formula (VI)

(VI)

[Structure of compound (VI): ketone $R^1R^2C=O$]

wherein $R^1$ and $R^2$ are independently selected from the group consisting of hydrogen, methyl, ethyl, n-propyl, iso-propyl, n-butyl, iso-butyl, sec-butyl, tert-butyl, n-pentyl, 2-pentyl, 3-pentyl, neopentyl, n-hexyl, 2-hexyl and 3-hexyl, or $R^1$ and $R^2$ are joined and, taken together with the carbon atom to which they are attached, form a 4- to 7-membered cycloalkyl ring.

9. The process of claim 7 wherein the compound of the formula (II) is used in a solution of a suitable organic solvent which solution is prepared by neutralization the hydrochloric acid salt of the compound of the formula (II) with a base.

10. The process of claim 7 wherein the compound of the formula (II) is dissolved in a suitable organic solvent, treated with an acid which is generated in situ by adding a protic substance and an acid precursor, precipitated as a salt of the compound of the formula (II), and neutralized by adding an aqueous solution of a base.

11. The process of claim 10 wherein the protic substance is an alcohol and the acid precursor is an acylchloride.

* * * * *